United States Patent [19]
Hughett et al.

[11] Patent Number: 5,827,279
[45] Date of Patent: Oct. 27, 1998

[54] KNIFE COUPLER MECHANISM FOR AN ENDOSCOPIC INSTRUMENT

[75] Inventors: J. David Hughett, Hamilton; Rudolph H. Nobis, Mason, both of Ohio

[73] Assignee: Ethicon Endo-Surgery, Inc., Cincinnati, Ohio

[21] Appl. No.: 761,411

[22] Filed: Dec. 6, 1996

[51] Int. Cl.⁶ .................................................. A61B 17/36
[52] U.S. Cl. .............................. 606/45; 606/51; 606/205
[58] Field of Search ........................... 606/41, 42, 45–52, 606/205–208

[56] References Cited

U.S. PATENT DOCUMENTS

| | | |
|---|---|---|
| 2,068,721 | 1/1937 | Wappler et al. . |
| 4,655,216 | 4/1987 | Tischer . |
| 5,174,300 | 12/1992 | Bales et al. . |
| 5,258,006 | 11/1993 | Rydell et al. . |
| 5,325,866 | 7/1994 | Kryzanowski ........................ 606/205 |
| 5,334,198 | 8/1994 | Hart et al. .............................. 6006/52 |
| 5,342,359 | 8/1994 | Rydell . |
| 5,403,342 | 4/1995 | Tovey et al. . |
| 5,445,638 | 8/1995 | Rydell et al. ........................... 606/51 |
| 5,458,598 | 10/1995 | Feinberg et al. . |
| 5,462,546 | 10/1995 | Rydell . |
| 5,527,313 | 6/1996 | Scott et al. ............................. 606/51 |
| 5,573,534 | 11/1996 | Stone . |
| 5,573,535 | 11/1996 | Viklund ................................. 606/51 |

*Primary Examiner*—Michael Peffley
*Attorney, Agent, or Firm*—Bernard Shay

[57] ABSTRACT

An electrosurgical instrument according to the present invention includes a handle, an elongated tube, an end effector, a pair of wireform conductors extending through the elongated tube from the handle to the end effector and a working tool such as, for example, a knife blade. The working tool being connected to the handle through a push bar which passes through the elongated tube. In an electrosurgical instrument according to the present invention, the push bar is positioned between the wireform conductors and is axially moveable with respect to the wireform conductors. In addition, in an electrosurgical instrument according to the present invention, the handle includes a coupling element to allow the wireform conductors and push bar to rotate with respect to the handle and to allow the push bar to move axially with respect to the wireform conductors and the handle.

2 Claims, 8 Drawing Sheets

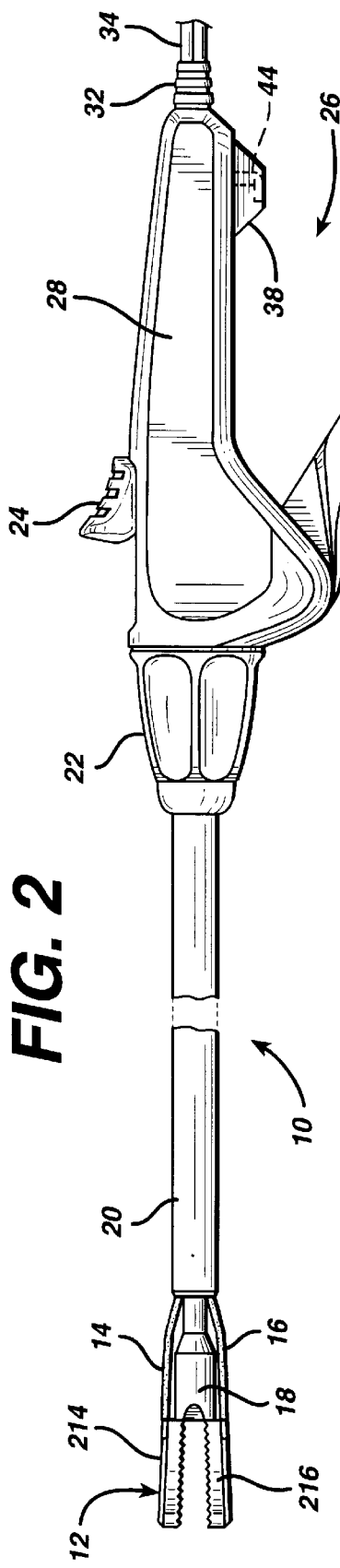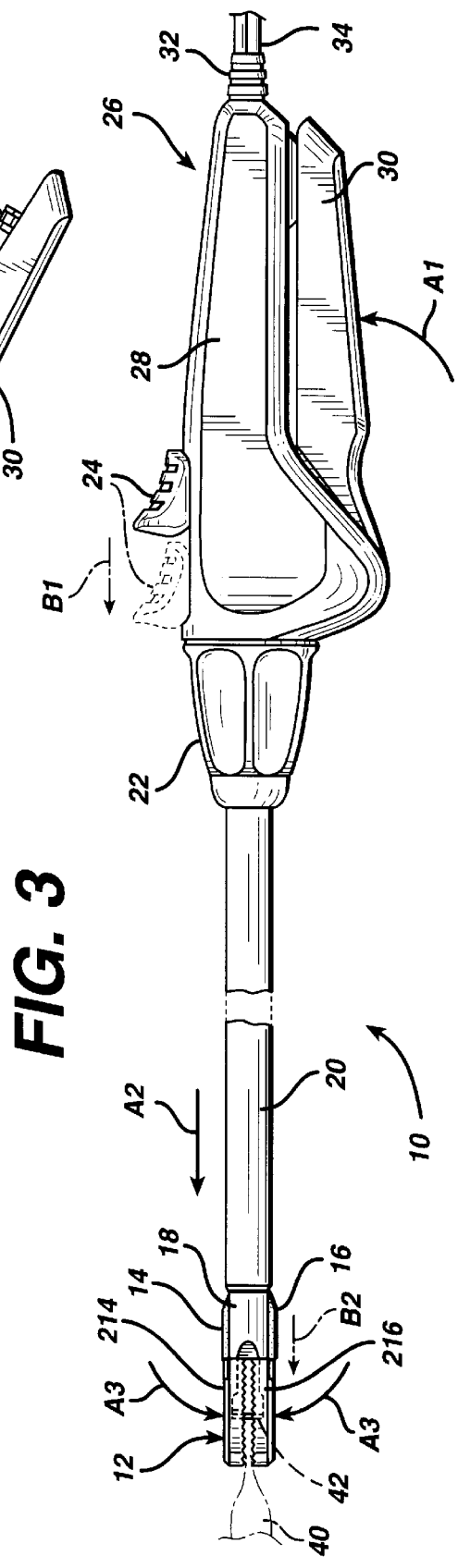

KNIFE COUPLER MECHANISM FOR AN ENDOSCOPIC INSTRUMENT

This application is related to the following copending patent applications: application Ser. No. 08/537,065, application Ser. No. 08/536,726, now U.S. Pat. No. 5,674,220, application Ser. No. 08/751,898, and application Ser. No. 08/555,741.

FIELD OF THE INVENTION

The present invention relates, in general, to a handle for use with electrosurgical instruments and, more particularly, to an improved coupling device for use with a handle for an electrosurgical instrument.

BACKGROUND OF THE INVENTION

Electrosurgical instruments are used by surgeons to apply electrosurgical energy to tissue. Electrosurgical devices are used for effecting improved hemostasis by heating tissue and blood vessels to cause coagulation or cauterization. Monopolar electrosurgical devices utilize one active electrode associated with the cutting or cauterizing instrument and a remote return or ground electrode which is usually attached externally to the patient. Thus, in surgery utilizing monopolar instruments, electrical current passes from the active electrode, through the patient to the return electrode. In bipolar electrosurgical instruments, both electrodes are included on the instrument and, generally, both electrodes are active. Thus a typical bipolar instrument includes two or more electrodes which are charged to different electrical potentials. In bipolar electrosurgical instruments, the tissue is treated by passing electrical current through tissue positioned between the electrodes.

Electrical energy is used in medical instruments for a number of purposes including hemostasis, that is to stop or slow bleeding in tissue. Application of electrical current in conjunction with pressure applied by the end effector of a surgical instrument results in a significant reduction in bleeding. Thus electrical current may be used to cauterize tissue prior to cutting the tissue, reducing or eliminating bleeding around the cut. The electrical current which passes through the tissue acts to heat the tissue. As the tissue is heated, it changes in color and texture. The experienced surgeon may, by looking for changes in the color or texture of the tissue around the end effector, determine when to turn off the current to the end effector. Once the tissue has been treated and the current turned off, the tissue grasped by the end effector may be cut, by, for example, advancing a knife blade through the end effector.

Bipolar forceps, being one type of bipolar electrosurgical instrument, have been used in various procedures for coagulating tissue. Generally bipolar forceps include two opposing jaws each connected to an output electrode of an electrical generator such that, when the generator is turned on, the opposing jaws are charged to different electrical potentials. Organic tissue being electrically conductive, the charged electrodes apply electrical current through the grasped tissue. Once the tissue has been treated to limit blood flow, a knife or other cutting instrument may be used to cut the tissue. In most such devices, the knife is positioned to travel through a knife channel in the instrument.

In many electrosurgical instruments, particularly those used with a trocar for endoscopic or laparoscopic procedures, it is advantageous to make the end effector rotatable with respect to the instrument handle so that the end effector may be rotated to reach structures within the body while maintaining the position of the handle. Further, in most such instruments, the cutting element moves axially independent of the end effector to cut tissue. It would be advantageous to design an electrosurgical instrument wherein the jaws of the end effector are supported by wireform type electrical conductors which extend from the handle to the end effector and conduct electricity to the end effector. It would also be advantageous to design an electrosurgical instrument including wireform electrical conductors wherein the end effector jaws, cutting element and wireform conductors rotate together with respect to the handle while the cutting element may be moved axially independent of the jaws and the wireform conductors.

SUMMARY OF THE INVENTION

An electrosurgical instrument according to the present invention includes a handle, an elongated tube, an end effector, a pair of wireform conductors extending through the elongated tube from the handle to the end effector and a working tool such as, for example, a knife blade at the end effector. The working tool being connected into the handle through a push bar which passes through the elongated tube. In an electrosurgical instrument according to the present invention, the push bar is positioned between the wireform conductors and is axially moveable with respect to the wireform conductors. In addition, in an electrosurgical instrument according to the present invention, the wireform conductors and push bar rotate with respect to the handle to allow the end effector to rotate with respect to the handle.

In an electrosurgical instrument according to the present invention, the handle includes a coupling element comprising a hub and a connector disposed within the hub. The connector includes a pair of legs and a bridge connecting the legs. The legs include elements such as hooks which are designed to grasp the push bar such that movement of the coupling element along the axis of the elongated tube moves the push bar along the axis of the elongated tube. Rotational movement of the coupling element results in rotational movement of the push bar. In addition, wireform conductors pass through the hub of the coupling element on either side of the connector, allowing the coupling element and push bar to move axially without moving the electrodes axially. Rotational movement of the coupling element, on the other hand, results in rotational movement of the wireform conductors in conjunction with rotational movement of the push bar. Thus, where the wireform conductors are connected to the end effector and the push bar is connected to the working tool, the working tool may be moved axially independent of the wireform conductors or end effector while the working tool moves radially in conjunction with the wireform conductors and the end effector.

In a further embodiment of an electrosurgical instrument according to the present invention, the handle includes a coupling element comprising a hub which includes first and second guide slots and a latch slot disposed between the first and second guide slots. The latch slot includes a rib element which is designed to grasp the push bar such that movement of the coupling element along the central axis of the elongated tube moves the push bar along the central axis of the elongated tube. Rotational movement of the coupling element results in rotational movement of the push bar. In addition, wireform conductors pass through the first and second guide slots of the hub on either side of the latch slot, allowing the coupling element and push bar to move axially without moving the electrodes axially. Rotational movement of the coupling element, on the other hand, results in rotational movement of the wireform conductors in conjunction with rotational movement of the coupling element and the push bar. Thus, where the wireform conductors are connected to the end effector and the push bar is connected to the working tool, the working tool may be moved axially independent of the wireform conductors or end effector while the working tool moves radially in conjunction with the wireform conductors and the end effector.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is a side elevational view of an electrosurgical instrument shown with the jaws of the end effector in a first, unclamped position.

FIG. 3 is a side elevational view of an electrosurgical instrument shown with the jaws of the end effector in a second, clamped position.

DETAILED DESCRIPTION OF THE INVENTION

Figure 1:
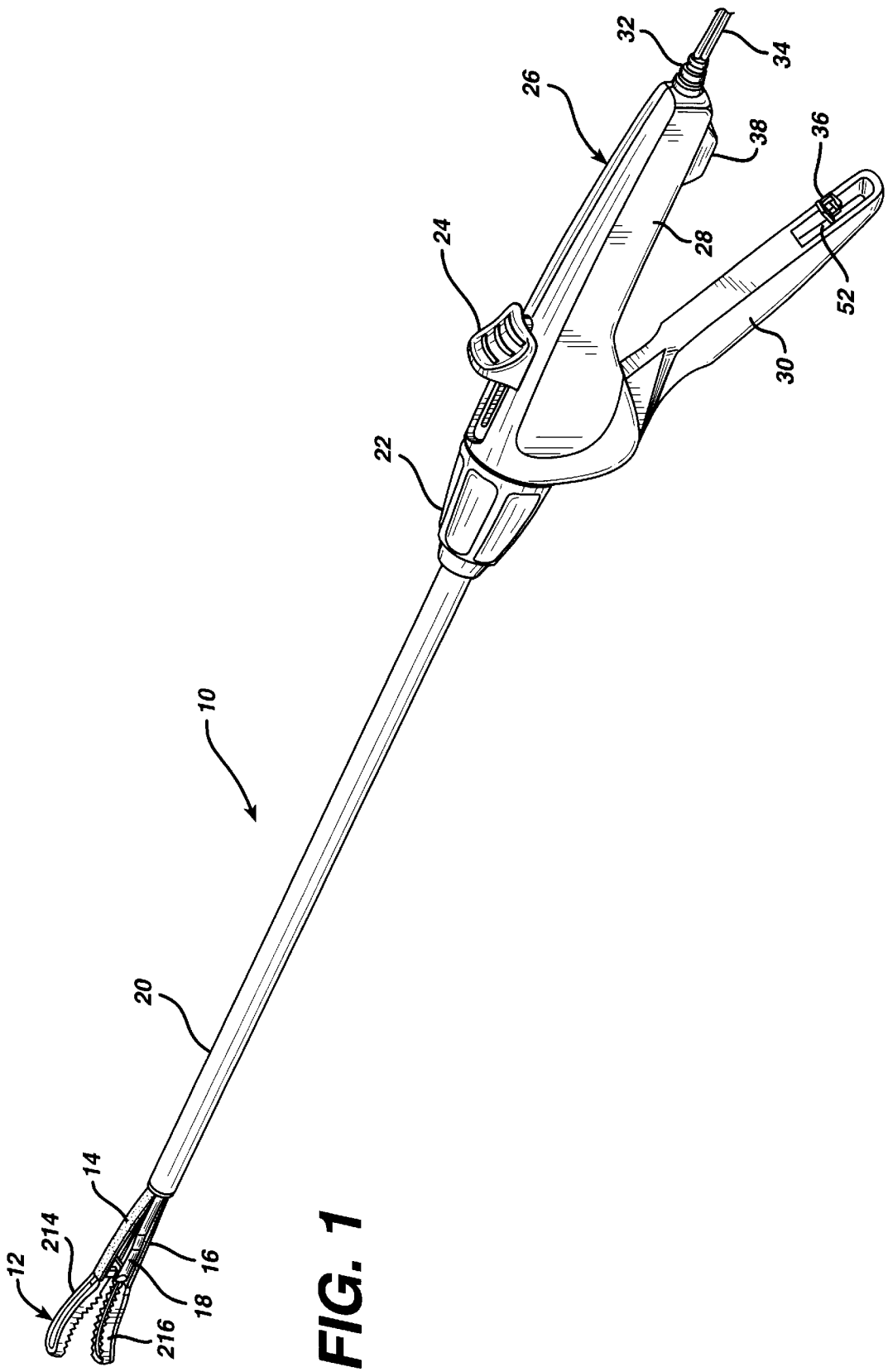
FIG. 1 is a perspective view of an electrosurgical instrument.

FIG. 1 is a perspective view of an electrosurgical instrument which may also be referred to herein as a bipolar forceps. In bipolar forceps 10, illustrated in FIG. 1, jaws 214 and 216 of end effector 12 are supported by upper wireform 14 and lower wireform 16. Wire forms 14 and 16 also act as electrical conductors, supplying bipolar electrical energy to end effector 12. Tissue stop 18 is positioned within tube 20. Tube 20 may be, for the present example, an elongated hollow closure tube extending from handle 26 toward end effector 12. Rotation knob 22 is indirectly attached to closure tube 20 to cause rotation of closure tube 20 and end effector 12 with respect to handle 26. Handle 26 includes knife button 24, grip 28 and trigger 30. Electrical cord 34 is connected to handle 26 through strain relief 32. Trigger latch 36 is positioned on trigger 30. Handle latch shield 38 is positioned on grip 28.

As illustrated in FIG. 2, bipolar forceps 10 has a first open position when trigger 30 is open. As illustrated in FIG. 3, the end effector 12 of bipolar forceps 10 has a second closed position when trigger 30 is in the closed position. Movement of trigger 30 in direction A1 moves closure tube 20 in direction A2 to force wireforms 14 and 16 together, forcing the jaws of end effector 12 in direction A3. In the closed position, as illustrated in FIG. 3, end effector 12 is adapted to grasp tissue 40. Movement of knife button 24 in direction B1 moves knife 42 in direction B2.

Figure 4:
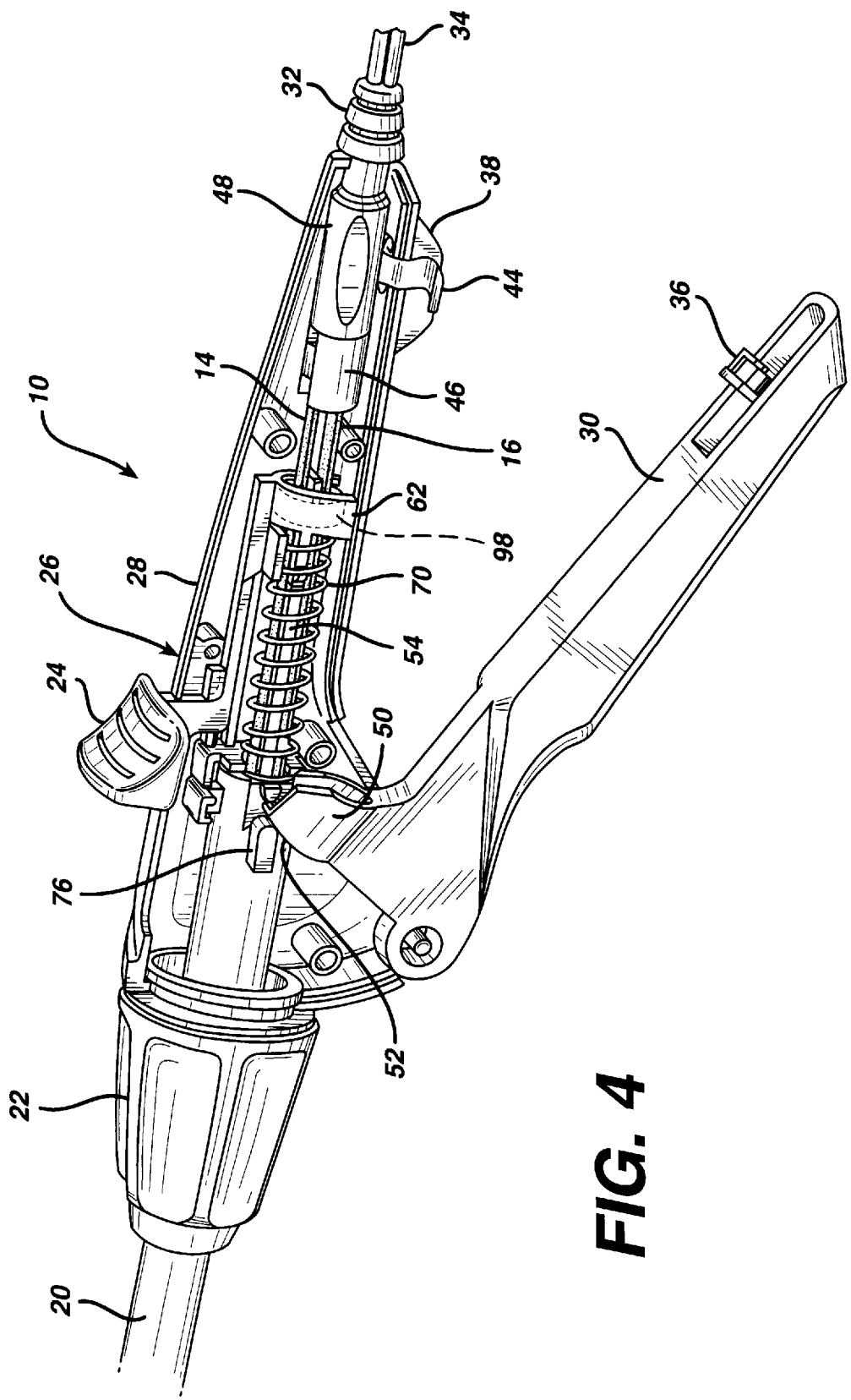
FIG. 4 is a perspective view of an electrosurgical instrument according to one embodiment of the present invention with the left side of the handle removed.

FIG. 4 is a perspective view of bipolar forceps 10 with the left side of grip 28 removed. In FIG. 4, handle latch 44 is illustrated. Wire form anchor 46, which is adapted to receive the proximal end of upper wireform 14 and lower wireform 16, is attached to interior strain relief 48 which in turn is a part of strain relief 32. Trigger yoke 50 on trigger 30 may include trigger yoke cam face 52.

Figure 5:
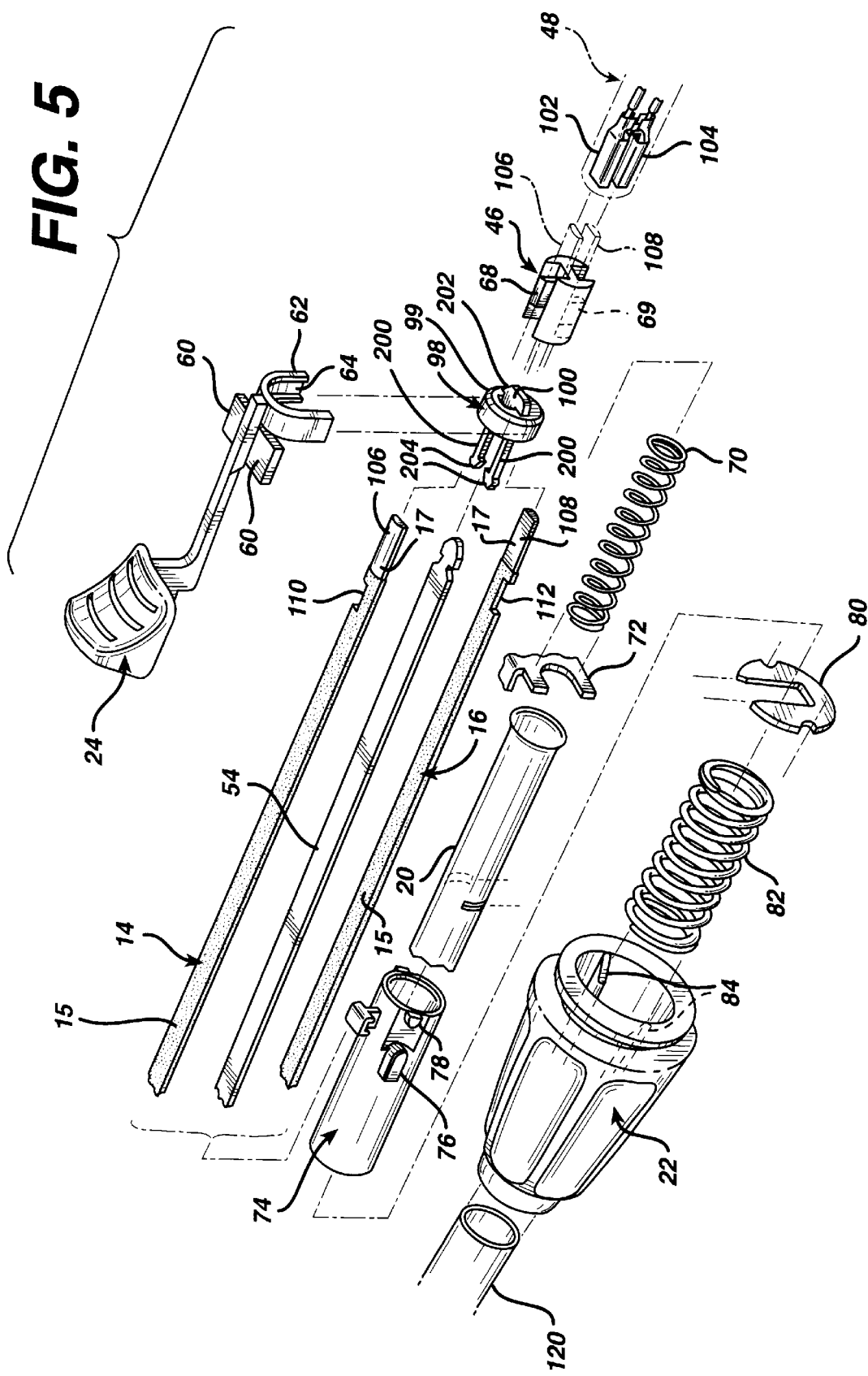
FIG. 5 is an exploded view of a portion of the internal mechanism of the handle illustrated in FIG. 4.

FIG. 5 is an exploded view of a portion of the internal mechanism of the handle illustrated in FIG. 4. In FIG. 5, the proximal end of push bar 54 is adapted to fit with connector 100 in hub 98. In the embodiment of the invention illustrated in FIG. 5, connector 100 and hub 98 cooperate to form coupler 99. Ribs 60 on knife button 24 are adapted to slide within the handle and guide knife button 24 as it moves axially along the handle 26. Yoke 62 of knife button 24 includes hub slot 64 which is adapted to receive knife hub 98. Rib 68 of wireform anchor 46 is adapted to fit within slots 110 and 112 of upper wireform 14 and lower wireform 16, respectively. Wireforms 14 and 16 each include insulation layer 15 and an electrical conductor 17. Knife return spring 70 works against knife spring retainer 72 to provide a counter force which counters the movement of knife button 24 in direction B1. Closure tube collar 74 is adapted to fit over the proximal end of closure tube 20 and includes drive rib 76 and retract rib 78, which interact with trigger yoke 50 as illustrated in FIG. 4. Closure tube washer 80 is adapted to fit within slots in closure tube 20 to hold closure tube collar 74 in place. Closure tube washer 80 also acts to retain trigger return spring 82. Closure tube washer 80 is guided axially by washer ribs 84 and rotation knob 22. Closure tube washer 80 also aids in keying wireform 16 wireform 18 and push bar 54 to rotation knob 22. Electrical connectors 102 and 104 are positioned within interior strain relief 48 and connected to upper wireform proximal connector 106 and lower wireform proximal connector 108 respectively to form an electrical connection between wireforms 14, 16 and chord 34. Slot 110 in upper wireform 14 and slot 112 in lower wireform 16 are adapted to mate with ribs 68 and 69, respectively, in wireform anchor 46. In FIG. 5, handle 26 of FIG. 4 includes coupler 99 comprising hub 98 and a connector 100 disposed within hub 98. Connector 100 includes a pair of connector legs 200 and a bridge 202 connecting connected legs 200. Connector legs 200 include hooks 204 which are designed to grasp the push bar 54 such that axial movement of coupler 99 moves push bar 54 along the axis of elongated tube 20. In addition, rotational movement of coupler 99 results in rotational movement of push bar 54. Wireforms 14 and 16 pass through hub 98 of coupling 99 on either side of connector 100, thus allowing coupler 99 and push bar 54 to move axially without moving wireforms 14 and 16 axially. Rotational movement of coupler 99, on the other hand, results in rotational movement of wireforms 14 and 16 in conjunction with push bar 54. Thus, where wireforms 14 and 16 are connected to jaws 214 and 216 of end effector 12 and push bar 54 is connected to a working tool such as knife 42, the working tool may be moved axially independent of wireforms 14 and 16 or end effector 12 while the working tool moves rotationally in conjunction with wireforms 14 and 16 and with end effector 12.

Figure 6:
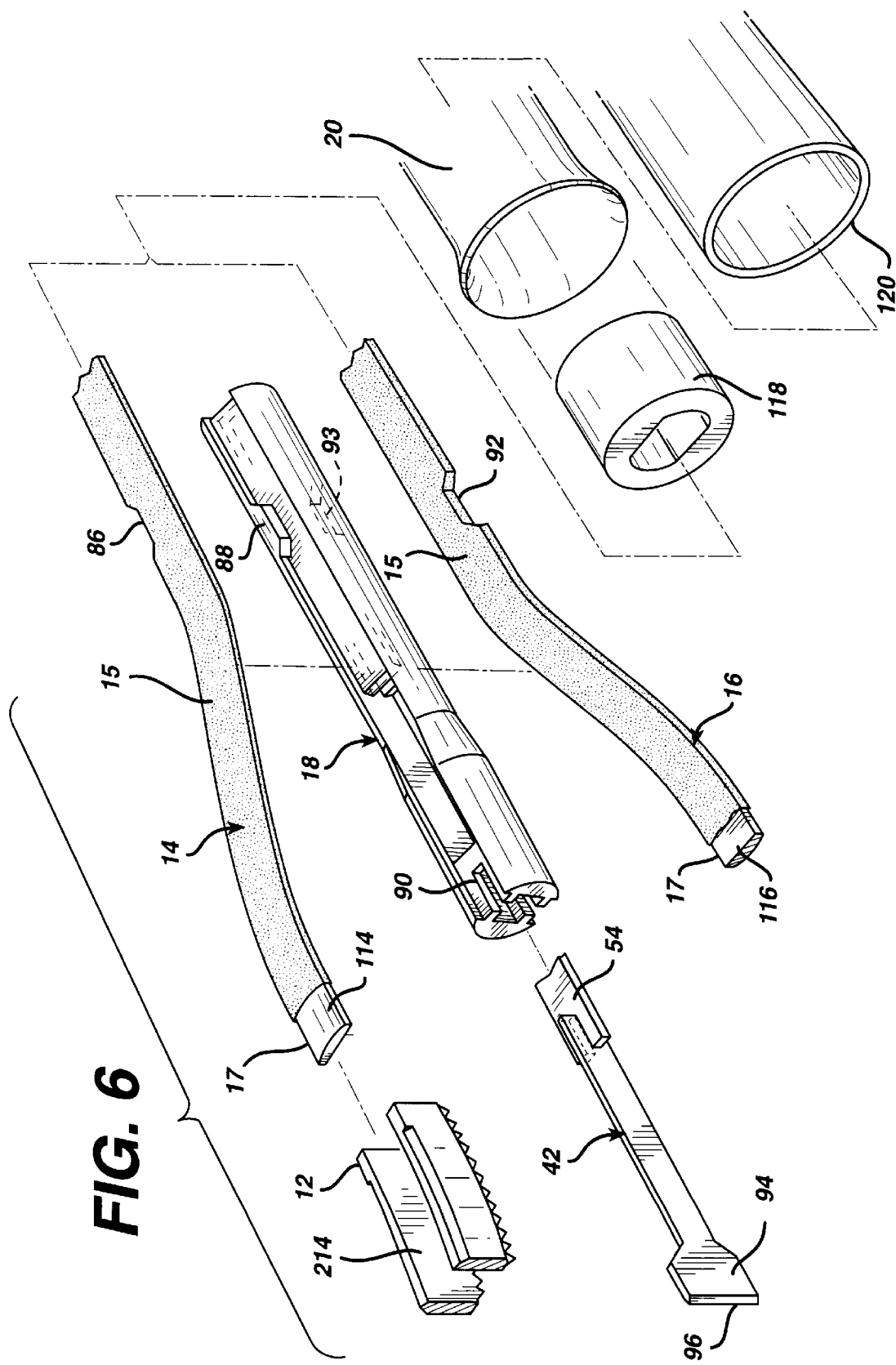
FIG. 6 is an exploded perspective view of a portion of the internal mechanism at the distal end of one embodiment of an electrosurgical instrument according to the present invention.

FIG. 6 is an exploded perspective view of the internal mechanisms of bipolar forceps 10 at the distal end of closure tube 20. In FIG. 6, upper wireform distal connector 114 may be soldered or welded to upper end effector jaw 214 to form a mechanical and electrical connection between jaw 12 and wireform 14. Similarly lower wireform distal connector 116 may be soldered or welded to lower end effector jaw 216 (not shown). Knife 42, which is connected to knife button 24 by push bar 54 and coupler 99, includes knife blade 94 and knife edge 96. Upper wireform 14 and lower wireform 16 pass through gas seal 118 which is positioned in the distal end of closure tube 20. Tissue stop 18 is positioned distal to gas seal 118. Closure tube 20 may be surrounded by an electrical insulator 120 such as shrink wrap tubing. Slot 86 in upper wireform 14 is adapted to mate with rib 88 in tissue stop 18. Similarly, slot 92 in lower wireform 16 is adapted to mate with rib 93 in tissue stop 18. Slot 90 in tissue stop 18 is adapted to receive knife blade 94 when knife button 24 is in its proximal position. Knife slot 90 acts to protect knife edge 96 of knife blade 94. Thus, tissue stop 18 may alternately be referred to as a knife guard.

Figure 7:
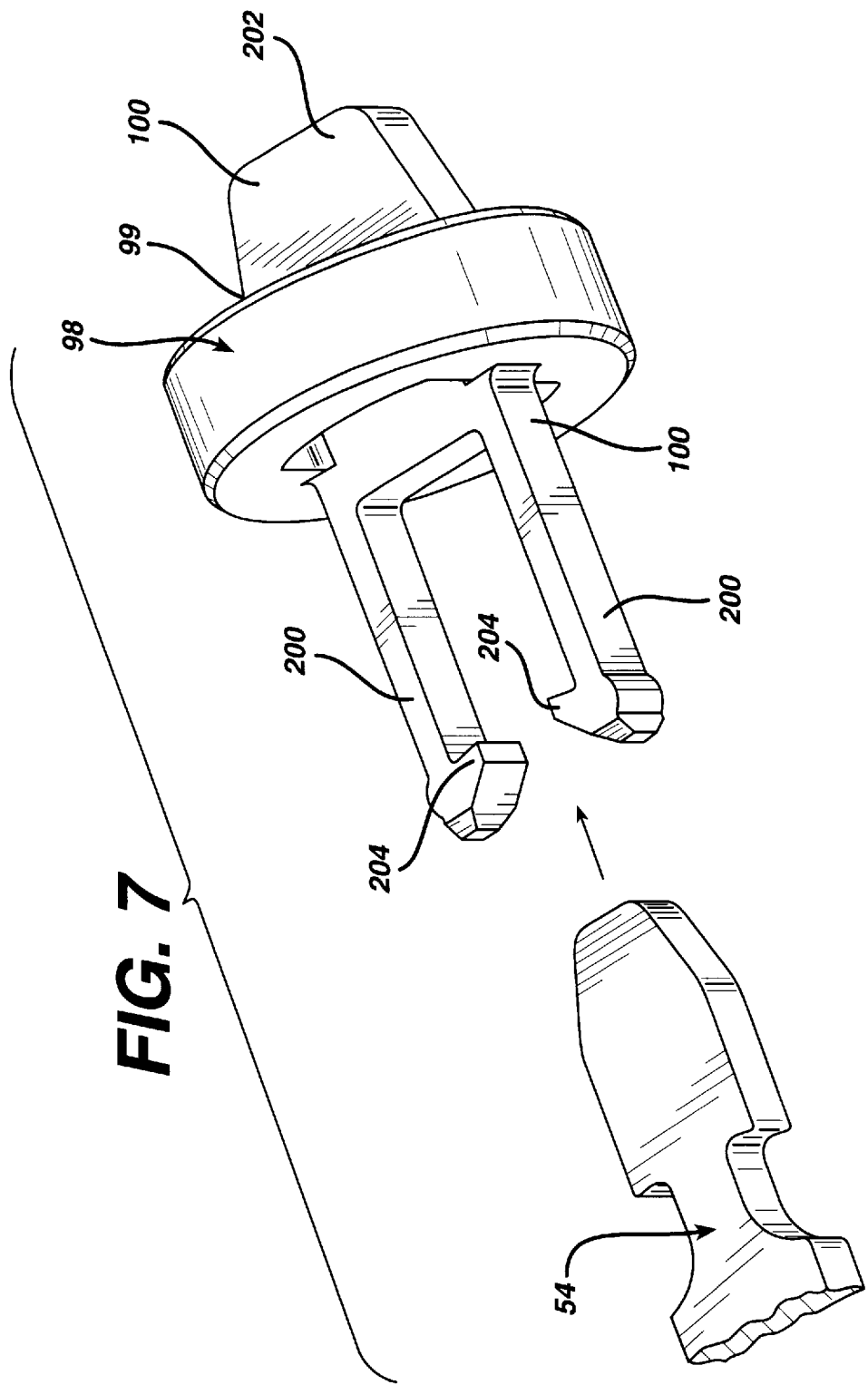
FIG. 7 is an exploded perspective view of a coupler and a push bar according to one embodiment of the present invention.
Figure 8:
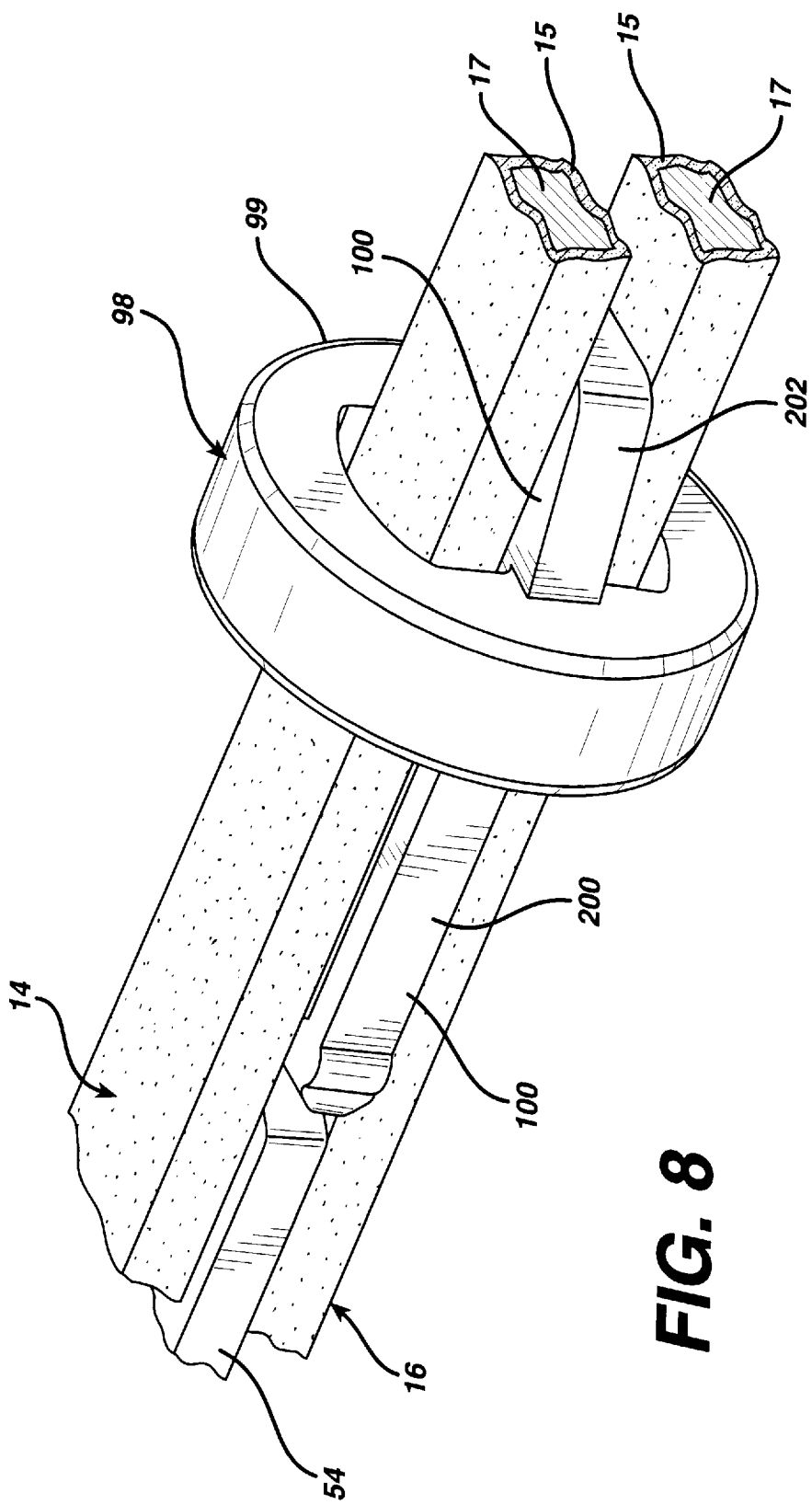
FIG. 8 is an perspective view of a coupler, push bar and wireform conductors according to one embodiment of the present invention.

FIG. 7 is a perspective side view of coupler 99 according to the present invention. In FIG. 7, push bar 54 is positioned to connect with connector legs 200 of coupler 99. FIG. 8 is a perspective view of coupler 99, assembled with push bar 54 and wireforms 14 and 16. In the embodiment illustrated in FIG. 8, coupler 99 and push bar 54 are adapted to rotate in conjunction with wireforms 14 and 16 while moving independently of wireforms 14 and 16 in a proximal to distal direction.

Figure 9:
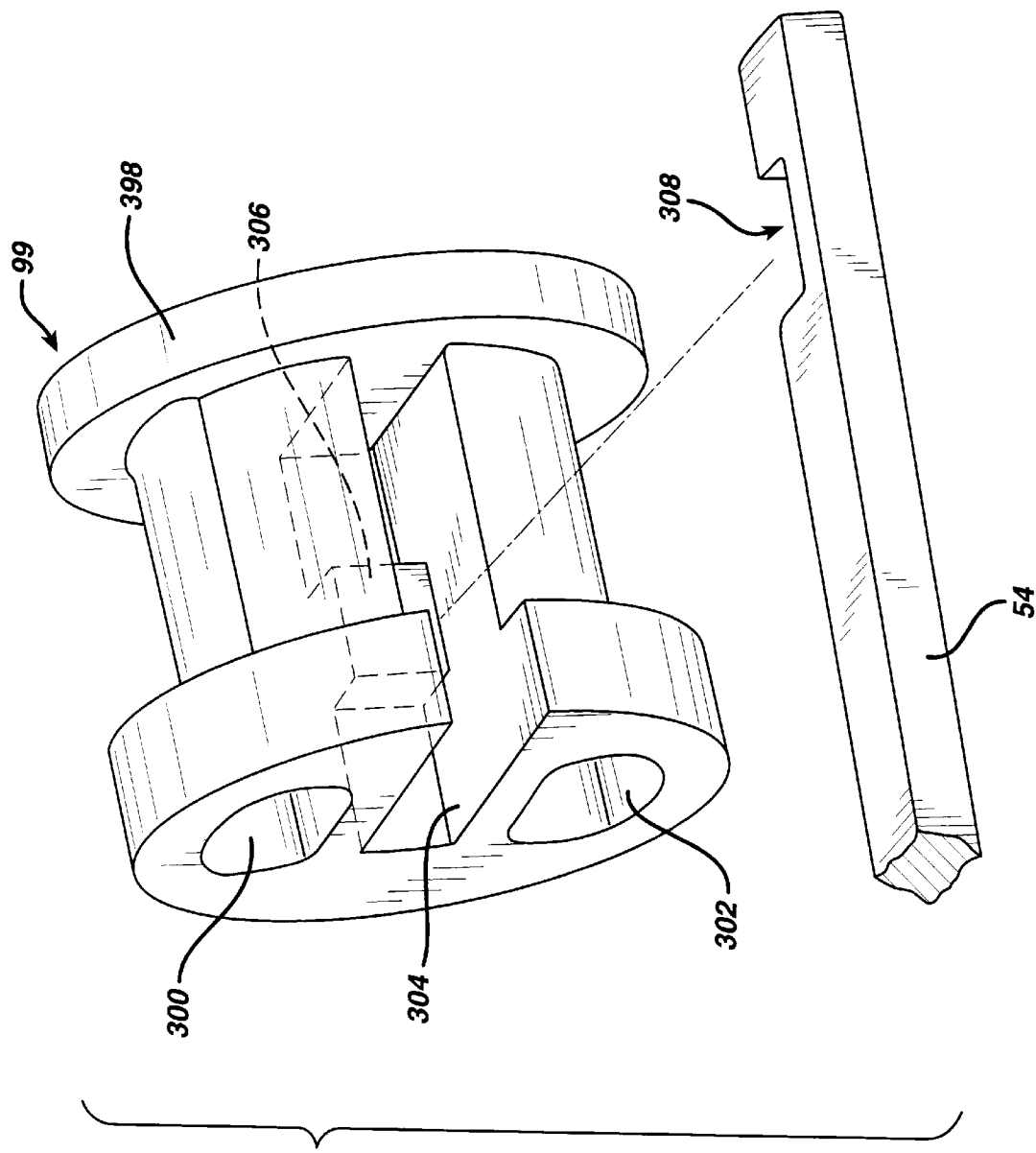
FIG. 9 is a side perspective view of a coupler according to one embodiment of the present invention.

FIG. 9 is a perspective view of a coupler 99 according to the present invention. In the embodiment illustrated in FIG. 9, hub 398 includes first guide slot 300, second guide slot 302 and latch slot 304. Latch slot 304 includes rib 306. Latch slot 304 is adapted to receive the proximal end of push bar 54 which to includes a slot 308 adapted mate with rib 306 in latch slot 304. In the connector illustrated in FIG. 9, guide slot 300 is adapted to allow wireforms 14 to pass freely through guide slot 300. Guide slot 302 is adapted to allow wireform 16 to pass freely through guide slot 302. Therefore, since push bar 54 is held securely in place by rib 306, rotational movement of connector 99 results in rotational movement of push bar 54 and rotation of wireforms 14 and 16. Axial movement of connector 99 results in axial movement of push bar 54 relative to wireforms 14 and 16. In the embodiment of the invention illustrated in FIGS. 4 and 5, hub 398 in FIG. 9 could be attached to a yoke such as yoke 62.

Referring now to FIGS. 2 and 3, the operation of a surgical instrument according to the present invention may be described. In FIG. 2, end effector 12 is open, knife button 24 is in its proximal position and trigger 30 is open. When trigger 30 is closed, as in FIG. 3, closure tube 20 slides forward over upper and lower wireforms 14 and 16, closing end effector 12. Knife 42 is deployed by moving knife button 24 from its proximal to its distal position in direction B1, thus cutting any tissue positioned within end effector 12. Handle latch 44 is adapted to hold trigger 30 in position until released, by, for example, squeezing trigger 30 a second time.

When trigger 30 is moved to its closed position, closure tube 20 is forced to its most distal position. Referring now to FIG. 4 and FIG. 5, as trigger 30 is closed, drive rib 76 moves along cam face 52. Drive rib 76 is forced against cam face 52 by the action of trigger return spring 82 which acts against closure tube washer 80 which engages closure tube 20 and closure tube collar 74. As trigger 30 is released, trigger return spring 82 forces closure tube collar 74 back by acting on closure tube washer 80. If for some reason closure tube 20 or end effector 12 becomes stuck, the interior face of trigger yoke 50 may be used to force closure tube collar 74 towards the proximal end of the instrument, thus opening the end effector. Handle latch 44 releasably engages trigger latch 36 such that by further pressure on trigger 30, latch 36 is released.

Referring now to FIGS. 4 and 5, knife button 24 is used to move knife blade 94. As knife button 24 is moved in a proximal to distal direction, yoke 62 moves in a proximal to distal direction. Coupler 99 being positioned in hub slot 64, the movement of yoke 62 in a proximal to distal direction moves coupler 99 in a proximal to distal direction. Coupler 99 being attached to push bar 54, movement of coupler 99 in a proximal to distal direction moves push bar 54 axially through closure tube 20 in a proximal to distal direction. Push bar 54 being connected to knife 42, movement of push bar 54 in a proximal to distal direction results in movement of knife 42 in a proximal to distal direction. Thus, movement of knife button 24 in a proximal to distal direction results in movement of knife 42 in a proximal to distal direction. Likewise, movement of knife button 24 in a distal to proximal direction results in movement of coupler 99, push bar 54 and knife 42 in a distal to proximal direction. Push bar 54 moves through closure tube 20 on a line which is substantially parallel to the central axis of closure tube 20. Wireform conductors 14 and 16, which are positioned on either side of push bar 54, pass through coupler 99 such that proximal to distal or distal to proximal movement of coupler 99 does not result in movement of either of wireform conductors 14 or 16.

Referring now to FIGS. 4, 5 and 6, rotation of rotation knob 22 results in rotation of end effector 12, including wireform conductors 14 and 16 and knife 42. When rotation knob 22 is turned or rotated, that rotational motion is transmitted to closure tube washer 80 which rotates closure tube 20. Closure tube 20 being connected to wireform conductors 14 and 16 through closure tube washer 80, rotational movement of closure tube 20 results in rotational movement of wireform conductors 14 and 16. Push bar 54, being positioned between wireform conductors 14 and 16 and attached to knife 42, rotational movement of wireform conductors 14 and 16 results in rotational movement of push bar 54 which, in turn, rotates coupler 99. Coupler 99 rotates freely within hub slot 64 of yoke 62 allowing push bar 54 rotate with wireform conductors 14 and 16.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical instrument comprising:
   a handle;
   an end effector operatively connected to said handle through an elongated tube;
   first wireform conductor means for transmitting electrical current to a first jaw of said end effector, wherein said first wireform conductor means extends from said handle to said jaw through said elongated tube;
   second wireform conductor means for transmitting electrical current to a second jaw of said end effector wherein said second wireform conductor means extends from said handle to said jaw through said elongated tube;

a knife means for cutting tissue, said knife means being moveable within said end effector;

button means on said handle for moving said knife means;

a push bar operatively connecting said knife to said button through a coupling means, wherein said first wireform conductor means passes through said coupling means on a first side of said push bar and said second wireform conductor means passes through said coupling means on a second side of said push bar and wherein said coupling means comprises:

a hub;

attachment means adapted to connect said coupling means to said push bar;

a connector disposed within said hub, said connector comprising first and second leg elements, and said attachment means comprising hook sections on said first and second leg elements.

2. An electrosurgical instrument according to claim 1 wherein said coupling element comprises:

a hub including first and second guide slots;

a latch slot disposed within said hub, between said guide slots, wherein said attachment means comprises a rib disposed within said latch slot.

* * * * *